United States Patent
Nakajima et al.

(10) Patent No.: US 10,034,909 B2
(45) Date of Patent: Jul. 31, 2018

(54) ANTIOBESITY AGENT CONTAINING WALNUT EXTRACT

(71) Applicants: Toshihiro Nakajima, Ooba-cho, Aoba-ku, Yokohama-shi, Kanagawa (JP); FMS CO, LTD., Niida, Kochi-shi, Kochi (JP)

(72) Inventors: Toshihiro Nakajima, Yokohama (JP); Satoko Aratani, Tokyo (JP); Naoko Yagishita, Yokohama (JP); Hidetoshi Fujita, Chofu (JP)

(73) Assignees: Toshihiro Nakajima, Yokohama-shi (JP); FMS CO, LTD., Kochi-shi (JP)

( * ) Notice: Subject to any disclaimer, the term of this patent is extended or adjusted under 35 U.S.C. 154(b) by 11 days.

(21) Appl. No.: 15/121,385

(22) PCT Filed: Feb. 27, 2015

(86) PCT No.: PCT/JP2015/055980
§ 371 (c)(1),
(2) Date: Sep. 27, 2016

(87) PCT Pub. No.: WO2015/129895
PCT Pub. Date: Sep. 3, 2015

(65) Prior Publication Data
US 2017/0106034 A1    Apr. 20, 2017

(30) Foreign Application Priority Data
Feb. 27, 2014  (JP) ................. 2014-037311

(51) Int. Cl.
*A61K 36/52* (2006.01)
*A61K 9/00* (2006.01)
*A23L 33/00* (2016.01)

(52) U.S. Cl.
CPC .............. *A61K 36/52* (2013.01); *A23L 33/30* (2016.08); *A61K 9/0053* (2013.01); *A61K 2236/33* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| CN | 101347572 A | 1/2009 |
|---|---|---|
| JP | 7-69912 A | 3/1995 |
| JP | 2004091464 A * | 3/2004 |
| JP | 2008-184383 A | 8/2008 |
| JP | 2011-207778 A | 10/2011 |

OTHER PUBLICATIONS

International Search Report of International Application No. PCT/JP2015/055980 completed May 25, 2015 and dated Jun. 2, 2015 (6 pages).
Useful Plants of the world, Kabushiki Kaisha Heibonsha, Aug. 25, 1989, 572 to 573.
Toshiyuki Fukuda et al., "Reactive oxygen species-scavenging effect of crude drug", Fragrance Journal, Aug. 15, 1995, 23(8), 75 to 81.
Chemical abstracts, 2007, 2007: 357899.
Walunt Polyphenol Catalog, ver. 2. 3, Oryza Oil & Fat Chemical Co., Ltd., Sep. 22, 2006.
Tetsuya Kawano et al., "Himan to Ensho to Sanka Stress", Allergology & Immunology, Oct. 15, 2013, 20(11), 1574 to 1584.
Chisayo Kozuka et al., "Sanka Stress to Metabolic Syndrome", Hormone Frontier in Gynecology, Jun. 1, 2012, 19(2), 125 to 130.
Shintei Wakan' yaku, 1st edition, Dec. 5, 1985, 527 to 528.
Igaku Hyakka, Dec. 8, 2009 URL: http://big5.wiki8.com/hutaoye_75073/.
Online DITN, Mar. 2013, No. 420. Editorial (1)-(2) URL: http://www.novonordisk.co.jp/DITN/2013/ditn0313.pdf.
Ingrid Wickelgren, "Obesity:how big a Problem?", 1998, Science; vol. 280; No. 5368; pp. 1364-1367.
Martina I. Lefterova et al., "New developments in adipogenesis", 2009, Trends in Endocrinology and Metabolism; vol. 20; No. 3, pp. 107-114.
Evan D. Rosen et al, "Adipocyte differentiation from the inside out", 2006, Nature Reviews; Molecular Cell Biology; vol. 7; pp. 885-896.

* cited by examiner

*Primary Examiner* — Susan Coe Hoffman
(74) *Attorney, Agent, or Firm* — Pyprus Pte Ltd

(57) ABSTRACT

To provide an antiobesity agent. An antiobesity agent containing an extract of walnut branches, shells, or leaves as an active ingredient.

5 Claims, 9 Drawing Sheets

N=5

| Treatment groups | Treatment groups |
|---|---|
| A-3 | husks (30) (50 mg/kg) |
| B-3 | branches (30) (50 mg/kg) |
| C | vehicle (p.o) |

N=5

Fig. 10B
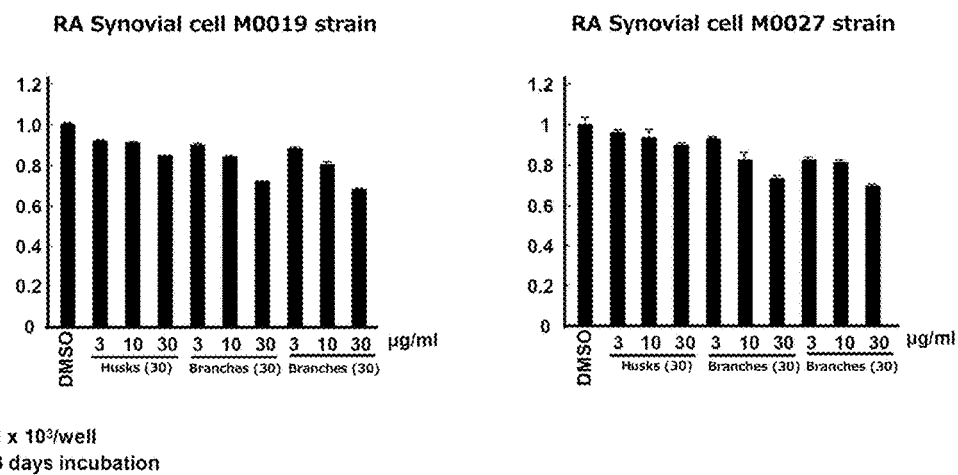
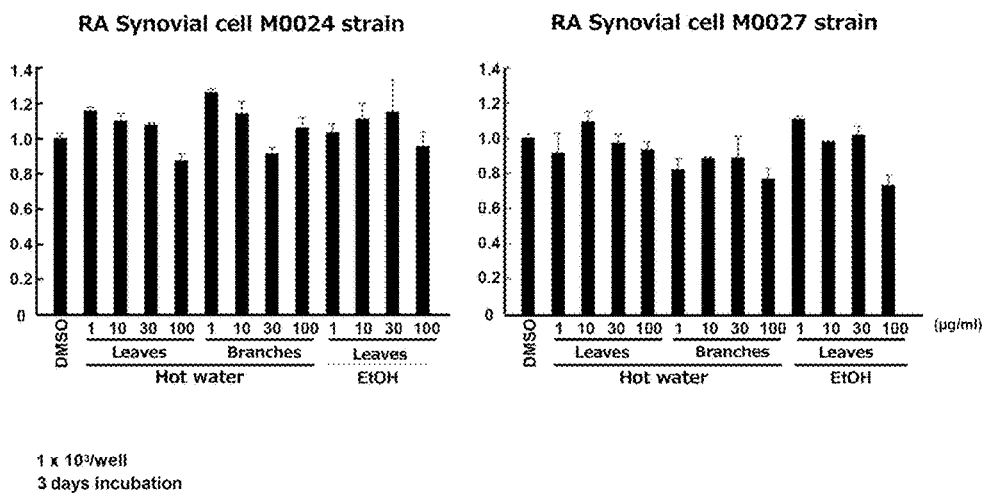
Fig. 10C

ANTIOBESITY AGENT CONTAINING WALNUT EXTRACT

TECHNICAL FIELD

The present invention relates to an antiobesity agent containing an extract of walnut. In particular, the present invention relates to an antiobesity agent for avoiding or preventing obesity by preventing an increase in neutral fat amount, cholesterol amount, fat amount, or body weight. It is considered that those working effects can be obtained as the antiobesity agent inhibits not only the binding between synoviolin and PGC-1β but also ubiquitination of PGC-1β by synoviolin.

BACKGROUND ART

In JP 2008-184383 A (Patent Literature 1), an agent containing polyphenol derived from walnut for treating or preventing hyperlipidemia or fatty liver is disclosed. In this Literature, it is described that the polyphenol component extracted from seed coat of walnut is effective for treatment of hyperlipidemia or fatty liver.

Obesity indicates a state in which an adipose tissue is excessively accumulated in a human body, and it may impose various high health risks such as diabetes, circulatory system disease, or depression (see, Non Patent Literature 1). In modern society, this problem causes very high economic and social losses. Molecular mechanism related to adipocyte metabolism has been broadly studied (see, Non Patent Literature 2 and Non Patent Literature 3).

Furthermore, a patient having a locomotive syndrome is on the rise in recent years. The patient having a locomotive syndrome has a problem in a locomotive organ, and thus there may be a case including a bed-bound state in which a care is needed.

CITATION LIST

Patent Literature

Patent Literature 1: JP 2008-184383 A

Non Patent Literature

Non Patent Literature 1: Wickelgren, I. (1998). Obesity: how big a problem? Science 280, 1364-1367.
Non Patent Literature 2: Lefterova, M. I., and Lazar, M. A. (2009). New developments in adipogenesis. Trends Endocrinol Metab 20, 107-114.
Non Patent Literature 3: Rosen, E. D., and MacDougald, O. A. (2006). Adipocyte differentiation from the inside out. Nat Rev Mol Cell Biol 7, 885-896.

SUMMARY OF INVENTION

Technical Problem

As described above, an antiobesity agent for avoiding or treating obesity is desired.

Furthermore, an agent for avoiding or treating a locomotive syndrome which is used for avoiding or treating a locomotive syndrome is needed.

Meanwhile, although it is described in Patent Literature 1 that components extracted from seed coat of walnut are effective for treatment of hyperlipidemia or fatty liver, it is not disclosed that they are effective for avoiding or treating obesity.

Under the circumstances, an object of the present invention is to provide an antiobesity agent. In particular, an object of the present invention is to provide an antiobesity agent for avoiding or preventing obesity by preventing an increase in neutral fat amount, cholesterol amount, fat amount, or body weight.

Solution to Problem

The aforementioned problems are solved by the invention described below.

A first aspect of the present invention relates to an antiobesity agent including an extract of walnut branches, shells, or leaves as an active ingredient.

The extract of branches, shells, or leaves of walnut is preferably an alcohol extract of branches, shells, or leaves of walnut. Particularly preferred is an alcohol extract of branches of walnut.

The antiobesity agent is preferably an agent for preventing an increase in neutral fat amount, cholesterol amount, fat amount, or body weight.

The extract of walnut branches, shells, or leaves is, for example, a material that is obtained by steps including:

a first heating reflux step in which 1 part by weight of walnut branches, shells, or leaves is admixed with 4 parts by weight or more and 30 parts by weight or less of an alcohol with concentration of 20 wt % to 60 wt % and the mixture is subjected at least once to heating reflux to obtain a first reflux liquid, a first filtering step in which the first reflux liquid obtained from the first heating reflux step is filtered to obtain a first filtrate and a first residue, a second heating reflux step in which 1 part by weight of the residue obtained from the first filtering step is admixed with 2 parts by weight or more and 20 parts by weight or less of an alcohol with concentration of 20 wt % to 60 wt % and the mixture is subjected at least once to heating reflux to obtain a second reflux liquid, a second filtering step in which the second reflux liquid obtained from the second heating reflux step is filtered to obtain a second filtrate, a first concentrating step in which the first filtrate is admixed with the second filtrate and then concentrated till to have sugar content of 5% or more and 40% or less to obtain a first concentrate, and a drying step in which the first concentrate admixed in the first concentrating step is dried to obtain a dry extract.

A second aspect of the present invention relates to an agent for avoiding or treating a locomotive syndrome including an extract of walnut branches, shells, or leaves as an active ingredient.

Advantageous Effects of Invention

As proven by Examples, the extract of walnut (in particular, extract of branches or shells) prevents in a significant sense an increase in neutral fat amount, cholesterol amount, fat amount, or body weight. It indicates that the extract of walnut is effective as an antiobesity agent.

Namely, according to the present invention, an antiobesity agent containing an extract of branches, shells, or leaves of walnut as an active ingredient can be provided. In particular, according to the present invention, an antiobesity agent for avoiding or preventing obesity by preventing an increase in neutral fat amount, cholesterol amount, fat amount, or body weight can be provided.

BRIEF DESCRIPTION OF DRAWINGS

FIG. 10B is a graph replacing the drawing which exhibits the influence of an extract of walnut on cell proliferation of synovial cells (M0019 strain, M0027 strain) that are derived from a patient with rheumatoid arthritis.

FIG. 10C is a graph replacing the drawing which exhibits the influence of an extract of walnut leaves and a hot water extract of walnut branches on cell proliferation of synovial cells (M0024 strain, M0017 strain) that are derived from a patient with rheumatoid arthritis.

DESCRIPTION OF EMBODIMENTS

Figure 1:
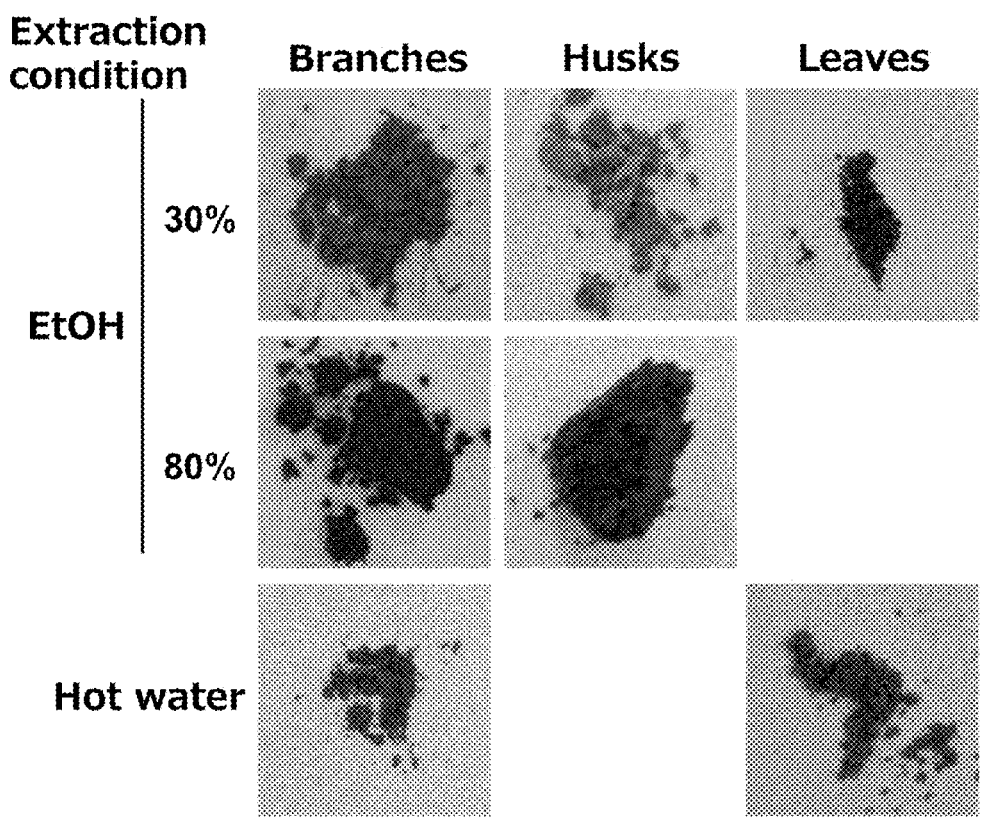
FIG. 1 is a photographic image replacing the drawing which exhibits the properties of an extract of walnut.

Hereinbelow, the modes for carrying out the present invention are described in view of the drawings. However, the present invention is not limited to the modes that are described below, and those resulting from, within an evident range, suitable modification of the modes by a skilled person in the art are also included in the present invention.

The first aspect of the present invention relates to an antiobesity agent containing walnut branches, shells, or leaves, or an extract of walnut branches, shells, or leaves as an active ingredient. In particular, the present invention relates to an antiobesity agent for avoiding or preventing obesity by preventing an increase in neutral fat amount, cholesterol amount, fat amount, or body weight. Preferred example of the present invention is an antiobesity agent which inhibits the binding between synoviolin and PGC-1β or an antiobesity agent which inhibits ubiquitination of PGC-1β by synoviolin.

Walnut is a well known tree and type of the walnut is not particularly limited. Examples of preferred walnut include onigurumi (*Juglans sieboldiana* Maxim), himegurumi (*Juglans subcordiformis* Dode), shinanogurumi (*Juglans regia* L.), and *Engelhardtia chrysolepis*. *Engelhardtia chrysolepis* is a tall evergreen tree which grows in mountain regions of southern China.

Branches of walnut include all of tree bark at walnut branch part, walnut branch from which tree bark has been removed, and tree bark of a walnut shaft. Among them, those preferred as the branches of walnut are tree bark at walnut branch part. The branches of walnut that are used in the present invention preferably have thickness of 1 mm or more and 10 cm or less. The thickness of a branch indicates a portion with the longest linear length within a cross-section of a branch. It is also possible that the thickness of a branch is 0.2 cm or more and 3 cm or less.

As for the branches of walnut, raw tree branches may be used directly or dried branches may be used. Furthermore, as for the branches of walnut, those obtained after shredding (that is, thinly-cut branches) may be used or those prepared in powder form may be used.

In general, branches of walnut contain a material which contains tannin, 5-hydroxy-1,4-naphtoquinone (juglone), 1,4,5-trihydroxy naphthalene (hydrojuglone), juglansin, carotene, inositol, pyrogallol, vitamin C, and a derivative thereof.

The shells of walnut indicate a flesh-removed seed part from which the core is further removed.

The extract of branches, shells, or leaves of walnut can be obtained by using branches, shells, or leaves of walnut as a raw material for extraction and extracting them with an extraction solvent which is water like cold water, warm water, or hot water; an organic solvent; or a mixture liquid of water and an organic solvent. Examples of the organic solvent which is used for the extraction include a single compound like a lower alcohol with 1 to 5 carbon atoms such as methanol, ethanol, propanol, isopropanol, or butanol; propylene glycol, 1,3-butylene glycol, acetone, methyl acetate, ethyl acetate, chloroform, toluene, pentane, hexane, cyclohexane, and heptane, or a combination of two or more of them. Preferred examples of the extraction solvent include water, a lower alcohol with 1 to 5 carbon atoms, a mixture liquid of the alcohol and water, and a mixture liquid of propylene glycol and water. The extract of walnut branches is preferably an alcohol extract of walnut branches. When branches, shells, or leaves of walnut are extracted with an alcohol, alcohol concentration is preferably 20 wt % or more and 60 wt % and less, and it may be 25 wt % or more and 35 wt % or less.

The method for extracting walnut branches is not particularly limited, and a cold immersion method, a warm immersion method, a percolation method, and other method commonly used for producing a plant extract may be widely used.

An extract of walnut is described in JP 4167849 B2, JP 5319522 B2, JP 2012-533597 A, and JP 2005-289999 A, for example, and in the present invention, an extract of walnut branches may be obtained by suitably using the methods described in those Literatures.

A preferred method for producing an extract of walnut is as follows. It is evident that, for producing an extract of walnut, conditions may be suitably adjusted or an optional step may be added. 1 part by weight of branches, shells, or leaves of walnut is admixed with 4 parts by weight or more and 30 parts by weight or less of an alcohol with concentration of 20 wt % to 60 wt % and the mixture is subjected at least once to heating reflux to obtain a first reflux liquid (that is, first heating reflux step). Concentration of the alcohol is preferably 20 wt % or more and 60 wt % or less, and it may be also 25 wt % or more and 35 wt % or less. Weight of the alcohol solution relative to 1 part by weight of branches, shells, or leaves of walnut may be 5 parts by weight or more and 20 parts by weight or less. It is preferable that the branches, shells, or leaves of walnut are cut as thin as possible. The heating reflux may be performed by appropriately using a known apparatus for reflux.

The first reflux liquid obtained from the first heating reflux step is filtered to obtain a first filtrate and a first residue (that is, first filtering step). As for the filtering method of the first filtering step, a well known filtering method may be suitably used.

1 part by weight of the residue obtained from the first filtering step is admixed with 2 parts by weight or more and 20 parts by weight or less of an alcohol with concentration of 20 wt % to 60 wt % and the mixture is subjected at least once to heating reflux to obtain a second reflux liquid (that is, a second heating reflux step). Concentration of the alcohol is preferably 20 wt % or more and 60 wt % or less, and it may be also 25 wt % or more and 35 wt % or less. Weight of the alcohol solution relative to 1 part by weight of branches, shells, or leaves of walnut may be 4 parts by weight or more and 15 parts by weight or less.

The second reflux liquid obtained from the second heating reflux step is filtered to obtain a second filtrate (that is, second filtering step).

The first filtrate is admixed with the second filtrate and then concentrated till to have sugar content of 5% or more and 40% or less to obtain a first concentrate (that is, first concentrating step). Method for concentrating a liquid is well known. The simplest method is a method in which a mixture liquid is heated and water content is reduced by evaporation.

The first concentrate obtained in the first concentrating step is dried to obtain a dry extract (that is, drying step). A well known drying method may be suitably employed as the method for drying. Examples of the drying step include spray drying.

The antiobesity agent of the present invention may be a pharmaceutical or a so-called supplement (nutrition supplement product). Furthermore, the antiobesity agent of the present invention may be a functional food product, a component of a functional food product, or a food additive like seasoning. Furthermore, the antiobesity agent of the present invention may be a cosmetic product for partial diet which is applied on a target area.

The antiobesity agent of the present invention is preferably an agent for preventing an increase in neutral fat amount, cholesterol amount, fat amount, or body weight. The agent for preventing an increase in neutral fat amount or cholesterol amount is an agent which can effectively prevent, in accordance with administration, a situation showing an increase in neutral fat amount or cholesterol amount. The agent for preventing an increase in fat amount is an agent which can reduce a fat amount in specific area or prevent a fat increase in accordance with administration. The agent for preventing an increase in body weight is an agent which can prevent an increase in body weight of a subject in accordance with administration.

The present invention also provides a method for preventing obesity of a subject in which an extract of branches, shells, or leaves of walnut is administered to a subject (for example, human or a mammal other than human) so that the subject can intake the extract of branches, shells, or leaves of walnut. The present invention also provides a method for preventing an increase in neutral fat amount, cholesterol amount, fat amount, or body weight of a subject in which the method includes the same step as above.

The extract of branches, shells, or leaves of walnut of the present invention is also effective for treatment of rheumatoid arthritis as proved by the examples. As such, the present invention is also effective as an agent containing an extract of branches, shells, or leaves of walnut as an active ingredient for treating or preventing rheumatoid arthritis. The present invention is particularly effective for a subject who suffers from rheumatoid arthritis and desires to have the antiobesity agent.

Rheumatoid arthritis is one of the reasons for having a locomotive syndrome. Locomotive syndrome is classified into a syndrome having a disorder of locomotive organ itself and a syndrome with dysfunction of a locomotive organ which is caused by aging. Among locomotive syndromes, examples of the disorder of a locomotive organ itself include arthrosis deformans, osteoporosis, and accompanying kyphosis, reverse-fracture type spondylosis, spondylosis deformans, and spinal stenosis. Further examples of the locomotive syndrome include a decrease in balancing performance, physical power, and locomotion capability which occurs in conjunction with an occurrence of pains, limited joint motion range, lowered muscle strength, paralysis, bone fracture, and stiffness as caused by rheumatoid arthritis. Further examples of the locomotive syndrome include a decrease in muscle strength, a decrease in endurance, delayed time for response, a decrease in motion speed, a decrease in manual dexterity, a decrease in deep sensation, and a decrease in balancing performance which are caused by physical performances that are deteriorated with aging. The extract of branches, shells, or leaves of walnut of the present invention is effective for prevention or treatment of a locomotive syndrome. As for the active ingredient, those described in the first aspect described above may be suitably employed. Hereinbelow, a pharmaceutical containing an extract of branches, shells, or leaves of walnut of the present invention is referred to as the agent of the present invention.

The agent of the present invention may be administered either orally or parenterally as a pharmaceutical composition after it is admixed with a physiologically acceptable carrier, vehicle, or diluent. As for the orally administered agent, it is possible to have a formulation like granules, powder, a tablet, a capsule, a soluble agent, an emulsion, and a suspension. As for the parenteral agent, a formulation like injection solution, a drop agent, an agent for external application, and a suppository may be selected. Examples of the injection solution include a hypodermal injection solution, an intradermal injection solution, and an intraperitoneal injection solution. Examples of the agent for external solution include an agent for intranasal administration, an inhalation agent (that is, spray agent), and an ointment. As for the formulation if it is used for prevention treatment of pulmonary fibrosis, an inhalation agent (that is, spray agent) is preferable from the viewpoint of having less side effects and lung-specific actions. A technique for formulation to have the aforementioned formulations containing the agent of the present invention as a main component is well known.

For example, a tablet for oral administration may be produced by adding and mixing the agent of the present invention with a vehicle, a disintegrant, a binder, a lubricant, or the like followed by tabletting with compression. As for the vehicle, lactose, starch, mannitol or the like are generally used. As for the disintegrant, calcium carbonate, calcium carboxymethyl cellulose, or the like are generally used. As for the binder, gum Arabic, carboxymethyl cellulose, polyvinyl pyrrolidone or the like are used. As for the lubricant, talc, magnesium stearate or the like are known.

Furthermore, the injection solution may be obtained by dissolving the agent of the present invention as a main component with a suitable dispersant, or dissolving or dispersing it in a dispersant. According to the selection of a dispersant, a formulation as an aqueous agent or an oily agent may be prepared. In order to have an aqueous agent, distilled water, physiological saline, or linger solution are used as a dispersant. Furthermore, for an oily agent, various plant oils or propylene glycol may be used as a dispersant. At that time, a preservative like paraben may be added, if necessary. Furthermore, to the injection solution, a known isotonic agent like sodium chloride and glucose may be added. Further, a pain-relieving agent like benzalkonium chloride and procaine hydrochloride may be added.

Furthermore, by preparing the agent of the present invention as a composition in solid state, liquid state, or semi-solid state, it is possible to provide it as an agent for external application. As the composition in solid state or liquid state is prepared as described above, it may be prepared as an agent for external application. A semi-solid composition may be prepared by adding, if necessary, a thickening agent to a suitable solvent. As for the solvent, water, ethyl alcohol, polyethylene glycol, or the like may be used. As for the thickening agent, bentonite, polyvinyl alcohol, acrylic acid, methacrylic acid, polyvinyl pyrrolidone, or the like may be used. To the composition, a preservative like benzalkonium chloride or the like may be added. Furthermore, as a carrier, an oily base like cacao butter or an aqueous gel base like cellulose derivatives may be combined to prepared a suppository.

A required amount (effective amount) of the agent of the present invention is administered, within a safe dose range, to a mammal including human. The dose of the agent of the present invention may be suitably set based on final determinations made by a physician or a veterinarian in consideration of types of a formulation, administration method, age or body weight of a patient, a symptom of a patient, or the like. Concentration of the dose of an extract of walnut branches may be suitably adjusted depending on the age of a subject, use, administration method or the like. For example, when the agent of the present invention is orally administered, it is sufficient that the extract of walnut branches is contained at 0.01 wt % or more and 10 wt % or less. Furthermore, the extract of walnut branches can be administered in an amount of 1 μg or more and 10 g or less per administration. Preferred amount of the extract of walnut branches is 5 μg or more and 5 g or less.

EXAMPLES

Preparation Example 1

A walnut extract (extract of walnut shells, extract of walnut branches, and extract of walnut leaves are collectively referred to as a walnut extract) was prepared according to the following order. 200 kg of walnut shells or walnut branches are admixed with 30% alcohol in an amount of 10 times (2000 liter), and an extraction processing based on heating reflux was performed for 2 hours. As for the walnut shells, a hard core part covering the seed (that is, walnut nucleolus) (edible part) was used, and as for the walnut branches, tree bark at walnut branch part and walnut branches from which tree bark has been removed were used. To remove plant residues from the mixture liquid, filtering was performed by using a 30 mesh followed by filtering using a 150 mesh to obtain the extraction solution A. The plant residues in mesh shape were admixed with 30% alcohol in an amount of 8 times (1600 liter), and an extraction processing based on heating reflux was performed again for 1 hour. When the reaction is completed, to remove plant residues from the mixture liquid, filtering was performed by using a 30 mesh followed by filtering using a 150 mesh to obtain the extraction solution B.

The extraction solution A and the extraction solution B were combined and, till to have sugar content (Brix value) of 10 to 20%, the first concentration was performed at concentration temperature of 60° C. or less. Next, the obtained temporary concentrate was subjected to the second concentration at concentration temperature of 60° C. or less till to have sugar content (Brix value) of 25 to 35%. To sterilize the secondary concentrate obtained therefrom, a sterilization process at 90° C. was performed for 1 hour two times.

Next, according to spray drying of the sterilized concentrate, a dry extract was obtained. The spray drying step was performed at conditions including entrance temperature of 140 to 230° C. and exit temperature of 80 to 100° C. The obtained dry extract was filtered through a 60 mesh and the obtained filtered product was prepared as a walnut extract (20 kg, yield: about 7%).

Preparation Example 2

A walnut extract was prepared in the same manner as Preparation Example 1 except that the extraction solvent of Preparation Example 1 is modified from 30% alcohol to 60% alcohol.

Preparation Example 3

A walnut extract was prepared in the same manner as Preparation Example 1 except that the extraction solvent of Preparation Example 1 is modified from 30% alcohol to 80% alcohol.

Properties of the walnut extract which has been prepared in the above Preparation Examples 1 and 3 are shown in FIG. 1. The walnut extract is powder as shown in FIG. 1, and as for the powder, the powder extracted with 30% alcohol is more favorable in terms of handling compared to the powder extracted with 80% alcohol.

Test Example 1

Figure 2:
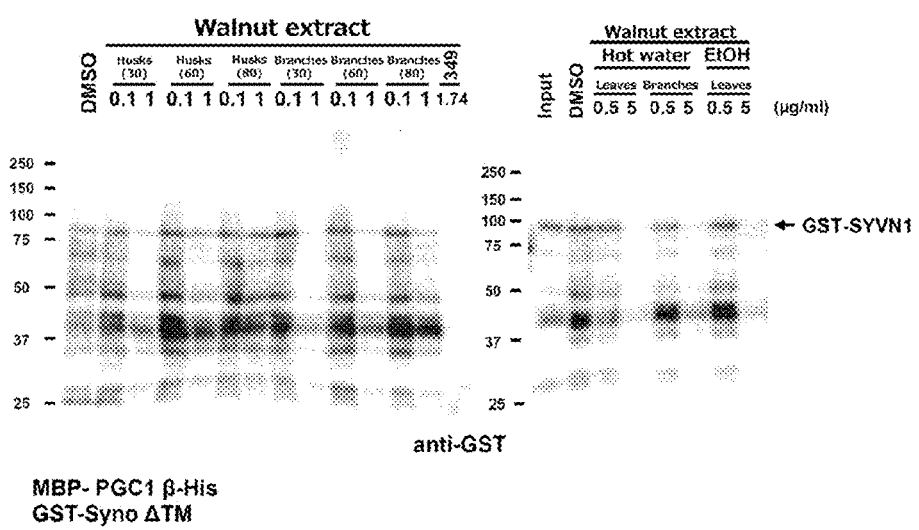
FIG. 2 is a photographic image replacing the drawing which exhibits the Western blot as a test result showing the inhibitory influence of an extract of walnut on binding between synoviolin and PGC-1β.

In order to investigate the activity of an extract of walnut for inhibiting the binding between synoviolin and PGC-1β, an in vitro binding analysis was performed. Furthermore, as a protein of this example, 0.4 μg of MBP-PGC-1β-His (MBP fused PGC-1β) and 2 μg of GST-Syno ΔTM (GST fused synoviolin with deleted transmembrane domain, see, JP 2008-74753 A) were used. 0.4 μg of MBP-PGC-1β His and 2 μg of GST-Syno ΔTM were allowed to bind to each other for 12 hours in a buffer (containing 20 mM Tris HCl pH 8.0; 100 mM NaCl, 1 mM EDTA, 0.1% NP-40, 1 mM DTT, 5% glycerol and protease inhibitor), and synoviolin was detected by using an anti GST antibody. The results are shown in FIG. 2. FIG. 2 is a Western blot which shows the effect of an extract of walnut for inhibiting the binding between synoviolin and PGC-1β. In FIG. 2, the shell 30, the shell 60, and the shell 80 indicate the extract of walnut shell which has been prepared in Preparation Example 1, Preparation Example 2, and Preparation Example 3, respectively. The branch 30, the branch 60, and the branch 80 indicate the extract of walnut branches which have been prepared in Preparation Example 1, Preparation Example 2, and Preparation Example 3, respectively. 349 indicates 5-hydroxy-1,4-naphtoquinone (synoviolin inhibitor, positive control).

From FIG. 2, it was found that the extract of walnut shells, extract of walnut branches, and extract of walnut leaves have an activity of inhibiting the binding between synoviolin and PGC-1β.

Test Example 2

Inhibition of Ubiquitination in Test Subject

Figure 3:
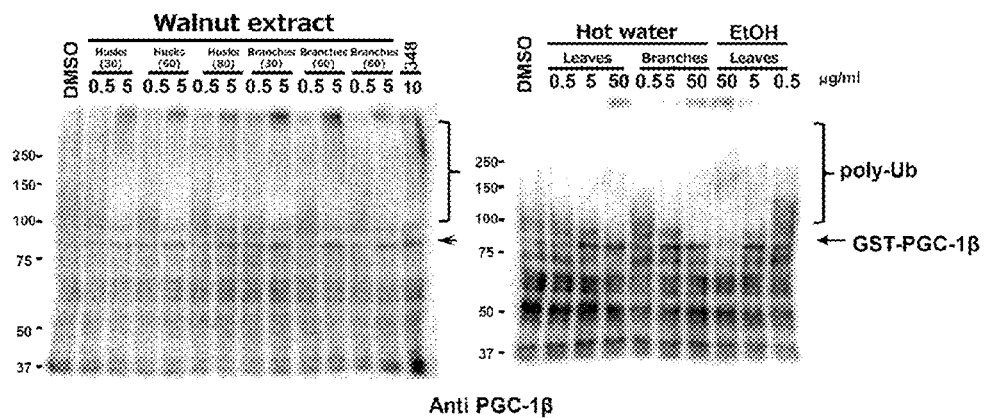
FIG. 3 is a photographic image replacing the drawing which exhibits the Western blot as a test result of in vitro ubiquitination assay.

In order to investigate the concentration dependency of an activity of a walnut extract for inhibiting ubiquitination of PGC-1β by synoviolin, an in vitro ubiquitination analysis was performed. As a protein of this example, GST-β5 (PGC-1β) and MBP-Syno ΔTM-His were used. The results are shown in FIG. 3. FIG. 3 is a Western blot which shows the concentration dependency of an activity of a walnut extract for inhibiting ubiquitination of PGC-1β. In FIG. 3, 348 indicates 5,8-dihydroxy-1,4-naphtoquinone (synoviolin inhibitor, positive control).

From FIG. 3, it was found that all the extract of walnut shells, extract of walnut branches, and extract of walnut leaves have a high activity of inhibiting the ubiquitination of PGC-1β.

Test Example 3

In Vivo Determination of Antiobesity Activity

Figure 4:
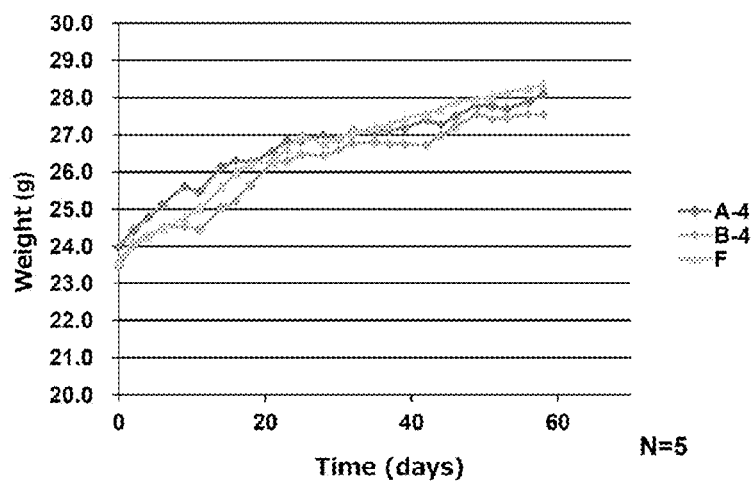
FIG. 4 is a graph replacing the drawing which exhibits the influence of an extract of walnut on a change in body weight of a wild type mouse.

By using a wild type mouse, determinations were made to see whether or not the administration of an extract of walnut induces a reduced body weight of a mouse. An extract of walnut (shell 30) and an extract of walnut (branch 30) of which concentration has been adjusted to 50 mg/ml using sterilized Milli Q was orally administered, each at a dose of 1 g/kg, to a 7 to 8 week-old wild type mouse, and the body weight of the mouse was measured every day. At a frequency of 3 times per every other week, administration was performed 25 times in total. As a control group, a solvent was administered to the wild type mouse as described above. The results are shown in FIG. 3. FIG. 4 is a graph illustrating the influence of an extract of walnut on a change in body weight of a wild type mouse. From FIG. 4, it was confirmed that the mouse administered with an extract of walnut shows reduced body weight compared to the control.

Test Example 4

Influence of Administration of Extract of Walnut on Food Intake Amount

Figure 5:
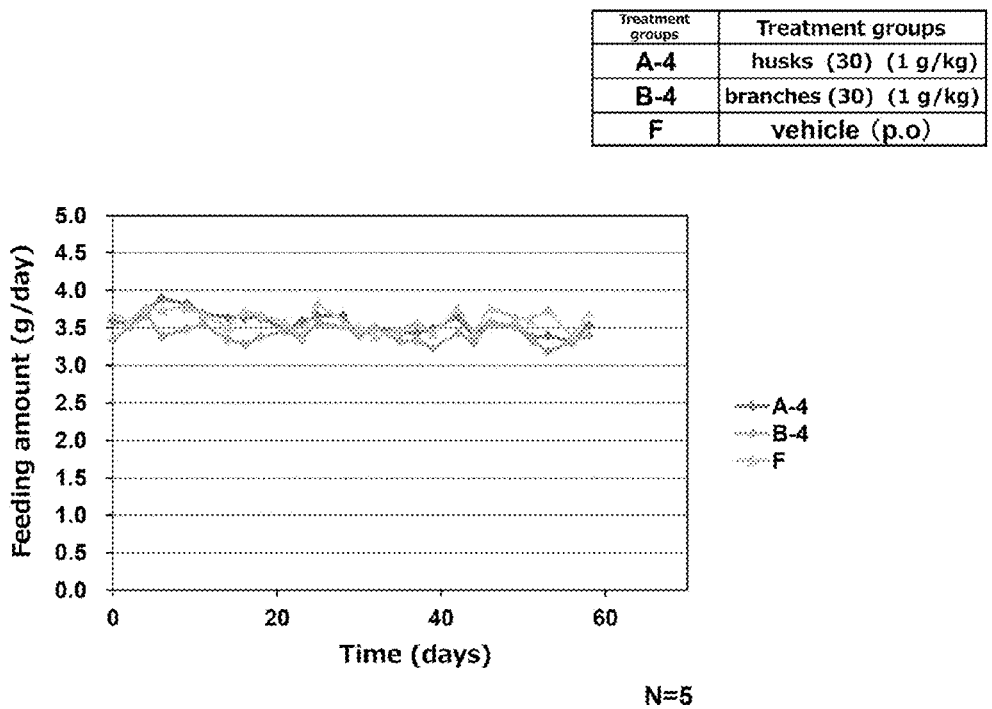
FIG. 5 is a graph replacing the drawing which exhibits the influence of an extract of walnut on an amount of food intake in a wild type mouse.

In order to investigate whether or not the reduced body weight of a mouse administered with a walnut extract is caused by reduced food intake amount, according to the procedures of Test Example 3, the food intake amount by a mouse was measured. The results are shown in FIG. 5. FIG. 5 is a graph illustrating the influence of an extract of walnut on an amount of food intake in a wild type mouse. From FIG. 5, it was found that there is no difference in food intake amount between the mouse administered with an extract of walnut and the control. Namely, it was shown that the reduced body weight is not caused by a reduced food intake amount.

Test Example 5

Determination of In Vivo Antiobesity Activity

By using a wild type mouse, determinations were made to see whether or not the administration of an extract of walnut under constant high-fat diet conditions can induce reduced body weight of a mouse.

Figure 6:
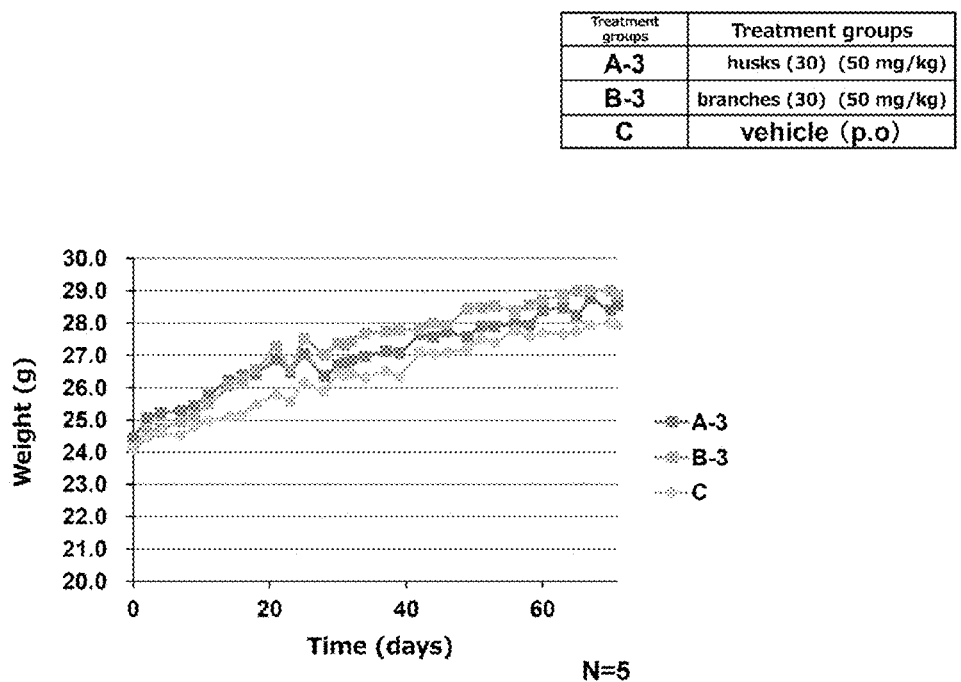
FIG. 6 is a graph replacing the drawing which exhibits the influence of an extract of walnut on a change in body weight of a wild type mouse.

An extract of walnut (shell 30) and an extract of walnut (branch 30) of which concentration has been adjusted to 50 mg/ml using DMSO and corn oil was orally administered, each at a dose of 50 mg/kg, to a 7 to 8 week-old wild type mouse, and the body weight of the mouse was measured every day. At a frequency of 3 times per every other week, administration was performed 31 times in total. As a control group, a solvent was administered to the wild type mouse as described above. The results are shown in FIG. 6. FIG. 6 is a graph illustrating the influence of an extract of walnut on a change in body weight of a wild type mouse. In FIG. 6, it was shown that, around 10 days after the start of the administration, the mouse administered with an extract of walnut exhibited an increase in body weight compared to the mouse of Comparative Example but the difference in body weight was not significant thereafter. Thus, it was found that the extract of walnut has an effect of preventing obesity against injection of oil and fat.

Test Example 6

Influence of Administration of Extract of Walnut on Food Intake Amount

Figure 7:
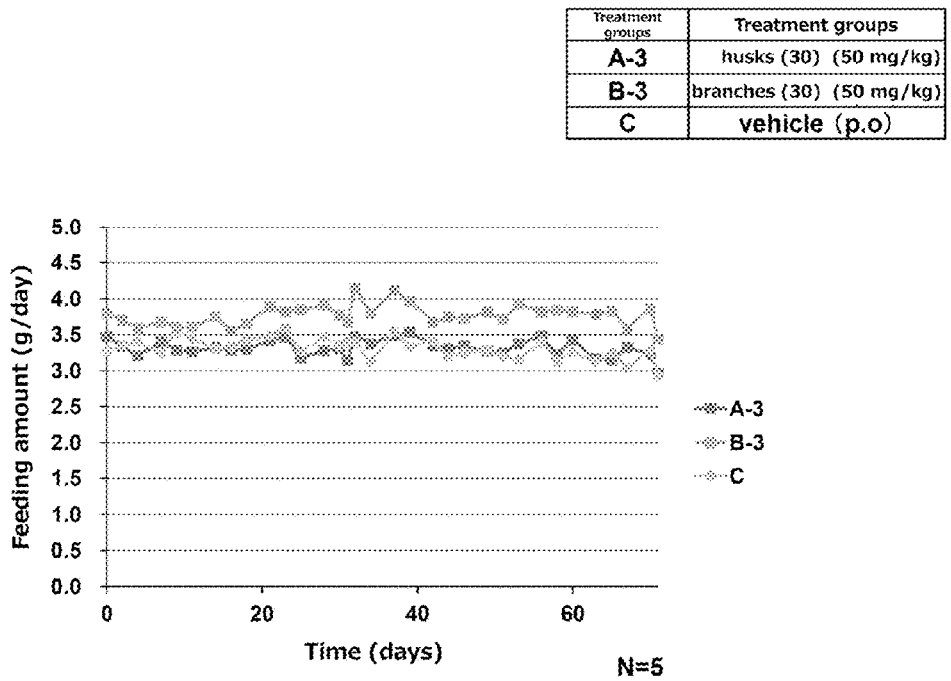
FIG. 7 is a graph replacing the drawing which exhibits the influence of an extract of walnut on an amount of food intake in a wild type mouse.

In order to investigate the relationship between an increase in body weight of a mouse administered with a walnut extract and the food intake amount, the food intake amount by a mouse at the time of carrying out Test Example 5 was measured. The results are shown in FIG. 7. FIG. 7 is a graph illustrating the influence of an extract of walnut on an amount of food intake in a wild type mouse. From FIG. 7, it was found that there is no difference in food intake amount between the shell 30 group and the control mouse. Meanwhile, from FIG. 7, it was found that the branch 30 group has a larger food intake amount than the subject mouse. Considering FIG. 6 and FIG. 7 together, it was found that, even though the food intake amount by the branch 30 group is higher than the subject mouse, the branch 30 group exhibited an inhibited body weight increase.

Test Example 7

In vivo Determination of Change in Weight of Epididymis Lipid

Figure 8:
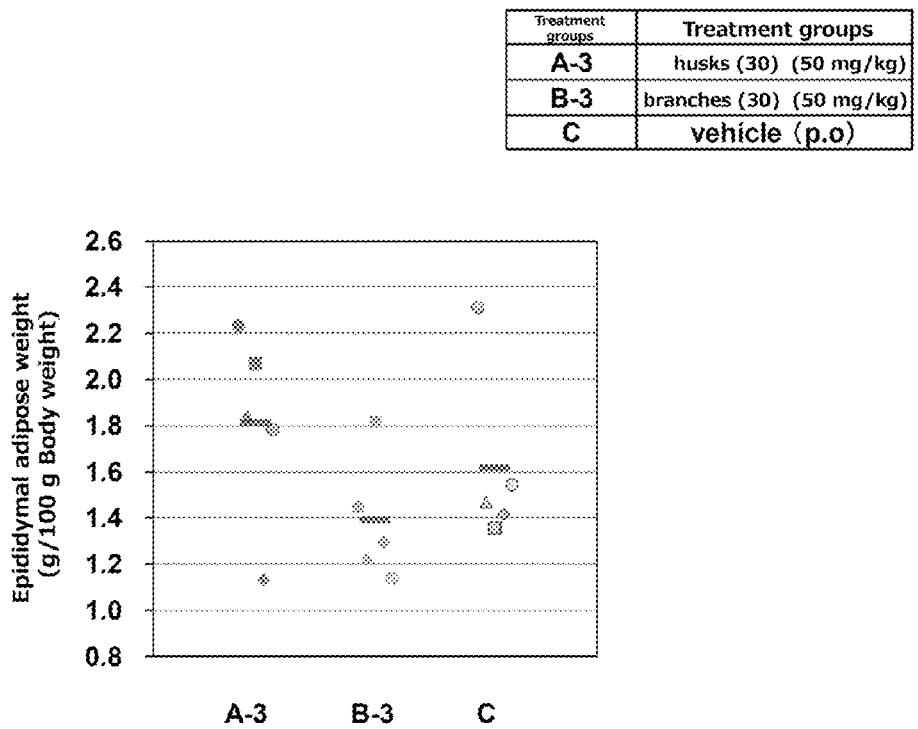
FIG. 8 is a graph replacing the drawing which exhibits the influence of an extract of walnut on a change in epididymis lipid weight in a wild type mouse.

By using a wild type mouse, determinations were made to see whether or not the administration of an extract of walnut can induce a decrease in weight of epididymis lipid of a mouse. Similar to Test Example 5, an extract of walnut (shell 30) and an extract of walnut (branch 30) of which concentration has been adjusted to 50 mg/ml using DMSO and corn oil was orally administered, each at a dose of 50 mg/kg, to a 7 to 8 week-old wild type mouse. At a frequency of 3 times per every other week, administration was performed 31 times in total. As a control group, a solvent was administered to the wild type mouse as described above. On Day 71 after starting the test, the mouse was dissected and the weight of epididymis lipid was measured. The results are shown in FIG. 8. FIG. 8 is a graph illustrating the influence of an extract of walnut on a change in epididymis lipid weight in a wild type mouse. In the graph, the weight of epididymis lipid per 100 g of body weight of a mouse on Day 71 was shown.

From FIG. 8 it was confirmed that, compared to the mouse group as a control group in which only the solvent is administered, the weight of epididymis lipid has decreased in the mouse group which has been administered with a walnut extract (branch 30). Namely, it was found that the extract of walnut (branch 30) has an effect of inhibiting an increase in epididymis lipid.

Test Example 8

Determination of Change in Blood Components

By using a wild type mouse, determinations were made to see whether or not the administration of an extract of walnut can induce a change in blood components of a mouse.

Figure 9A:
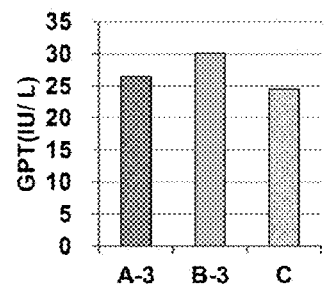
FIG. 9A is a graph replacing the drawing which exhibits the influence of an extract of walnut on a change in blood components in a wild type mouse (GOT, GPT, ALP).
Figure 9A:
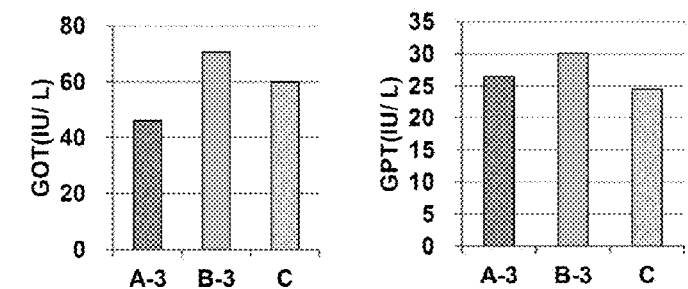
Figure 9A:
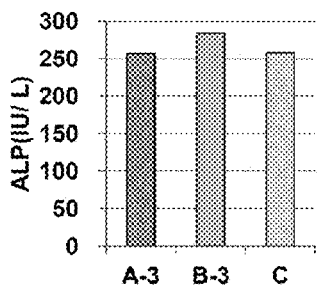
Figure 9B:
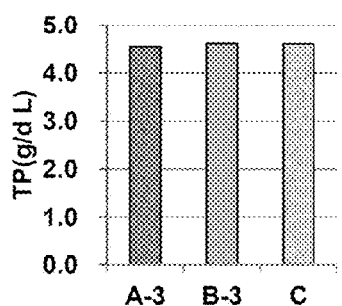
FIG. 9B is a graph replacing the drawing which exhibits the influence of an extract of walnut on a change in blood components in a wild type mouse (TP, ALB, BUN, UA).
Figure 9B:
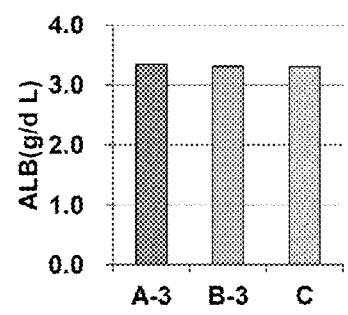
Figure 9B:
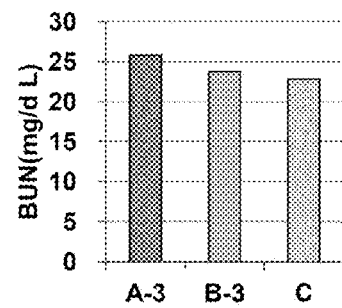
Figure 9B:
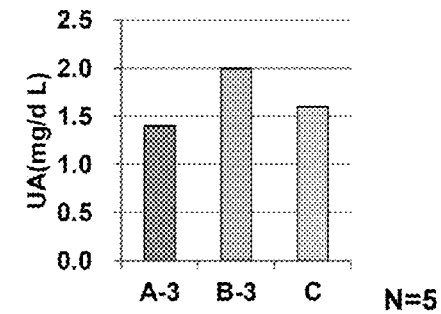
Figure 9C:
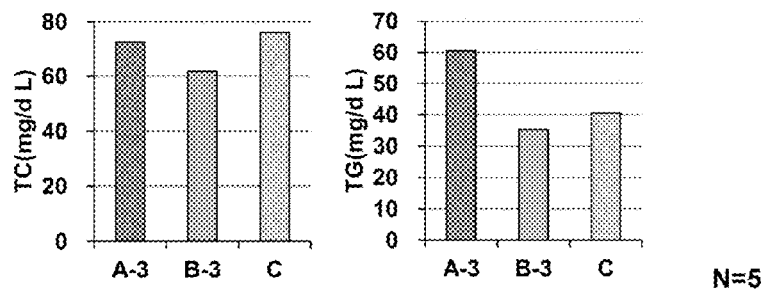
FIG. 9C is a graph replacing the drawing which exhibits the influence of an extract of walnut on a change in blood components in a wild type mouse (TC, TG).
Figure 9D:
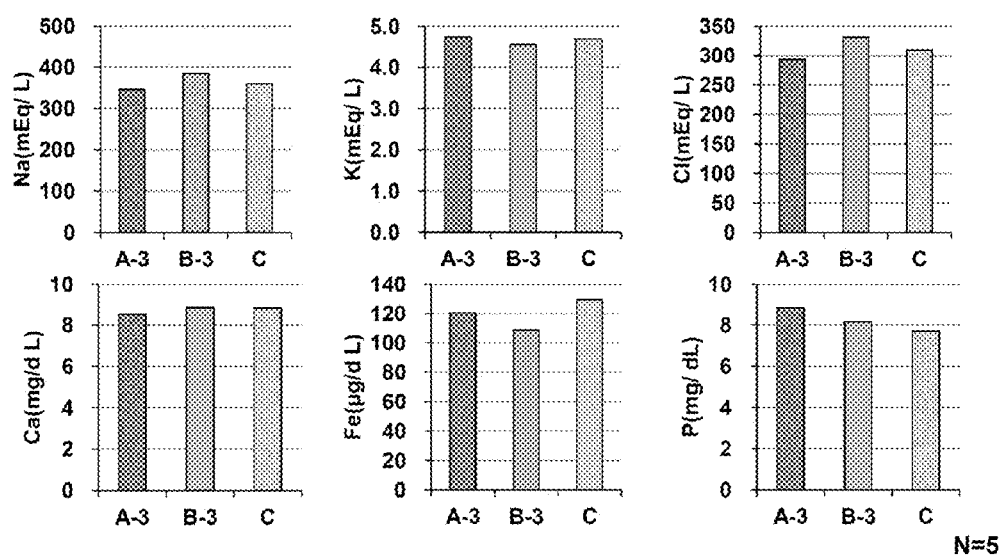
FIG. 9D is a graph replacing the drawing which exhibits the influence of an extract of walnut on a change in blood components in a wild type mouse (Na, K, Cl, Ca, Fe, P).
Figure 9E:
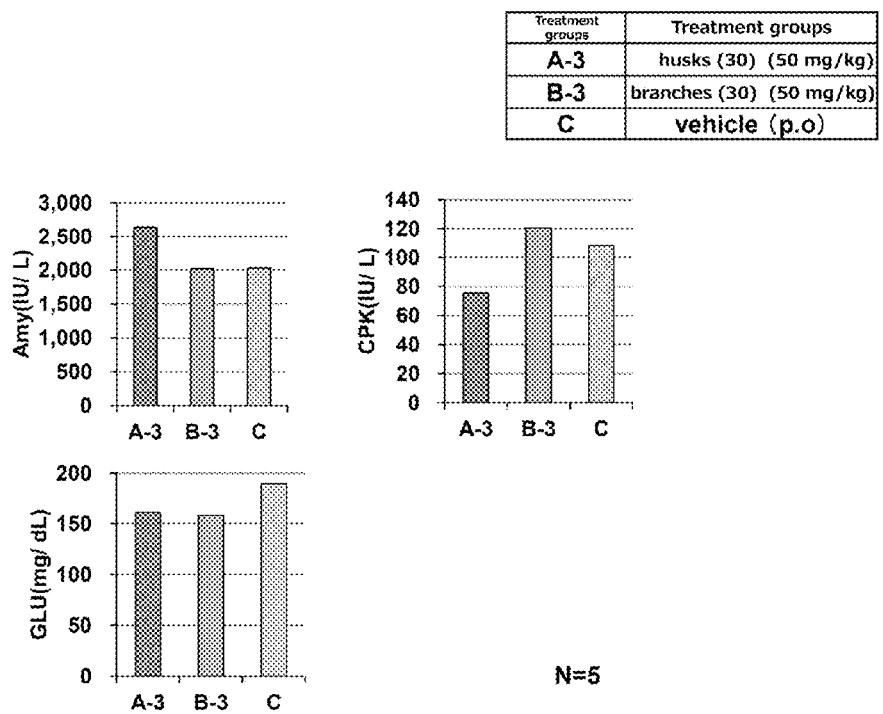
FIG. 9E is a graph replacing the drawing which exhibits the influence of an extract of walnut on a change in blood components in a wild type mouse (Amy, CPK, GLU).

Specifically, at the time of performing Test Example 7, blood was taken from a mouse on Day 71 after starting the test, and concentration of the components in blood serum (GOT, ALP, GPT, TP, BUN, ALB, UA, TC, TG, Na, Ca, K, Fe, Cl, P, Amy, GLU, CPK) was determined. The results are shown in FIGS. 9A to 9D. FIGS. 9A to 9D are a graph replacing the drawing which exhibits the influence of an extract of walnut on a change in blood components in a wild type mouse. FIG. 9A represents the amount of GOT (asparaginic acid aminotransferase), GPT (alanine aminotransferase), and ALP (alkali phosphatase) in blood. FIG. 9B represents the amount of TP (total protein), ALB (albumin), BUN (urea nitrogen), and UA (urea acid) in blood. FIG. 9C represents the TC (total cholesterol value), and TG (amount of neutral fat: amount of triglyceride) in blood. FIG. 9D represents the amount of Na, K, Cl, Ca, Fe, and P in blood. FIG. 9E represents the amount of Amy (amylase), CPK (creatine phosphokinase), and GLU (glucose) in blood.

From FIG. 9C, it was shown that a decrease in total cholesterol value or neutral fat amount is shown in the branch 30 group, in particular. Considering that the food intake amount is higher in the branch 30 group compared to the control, it is found that the branch 30 has an effect of lowering the total cholesterol value or neutral fat amount.

Comparative Example 1

By using an alcohol with plural kinds of concentration as described above, an extract of walnut flesh and an extract of seed coat of walnut were obtained. Except that an extract of walnut flesh and an extract of seed coat of walnut are used, the test was performed in the same manner as Test Example 5 to Test Example 8. As a result, it was found that the extract of walnut branches exhibits a significant effect on the total cholesterol value, neutral fat amount, fat amount, and an increase in body weight compared to an extract of walnut flesh and an extract of seed coat of walnut.

Test Example 9

Effect of Extract of Walnut for Inhibiting Proliferation of Synovial Cells

Figure 10A:
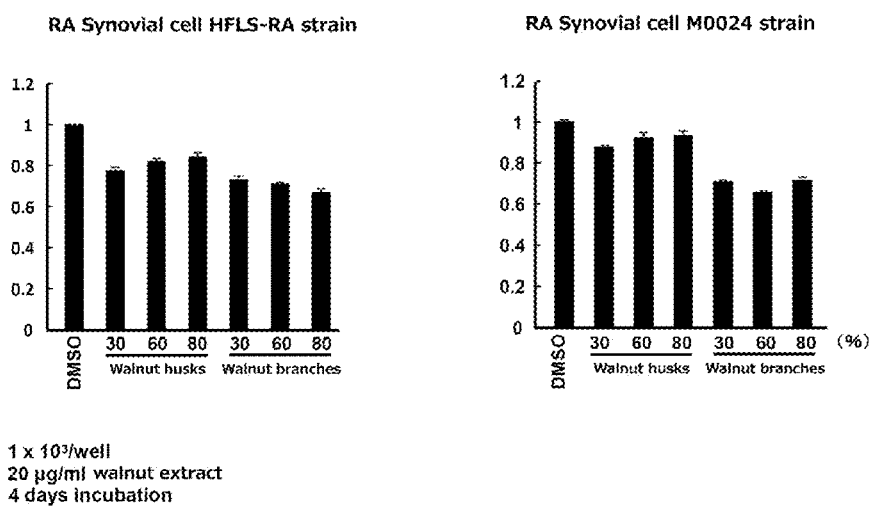
FIG. 10A is a graph replacing the drawing which exhibits the influence of an extract of walnut on cell proliferation of synovial cells (HFLS-RA strain, M0024 strain) that are derived from a patient with rheumatoid arthritis.

The effect on proliferation of synovial cells derived from a patient with rheumatoid arthritis was determined according to the following method. Synovial cells were seeded to a 96 well plate at $1 \times 10^3$/well, and after 6 to 24 hours, a walnut extraction solution or DMSO was added so as to have 20 μg/ml. 4 Days later, cell proliferation was measured by using Cell Counting Kit-8 (Dojindo). The results are shown in FIGS. 10A to 10C. The vertical axis indicates the relative value when the proliferation of synovial cells under addition of DMSO is set at 1. From the drawing, it was found that the proliferation of synovial cells was inhibited by 60 to 80% by the extract of walnut compared to the control. Furthermore, by adding the extract of walnut at 3, 10, 30, and 100 μg/ml to the synovial cells, concentration dependency was examined. As shown in FIGS. 10A to 10C, it was demonstrated that proliferation of synovial cells is inhibited by a walnut extraction solution in a concentration dependent manner.

Test Example 10

Therapeutic Effect of Extract of Walnut for Rheumatoid Arthritis

In view of the method by Kuzuna et. al. [Chem. Pharm. Bull., 23, 1184-1191(1975)], the therapeutic effect of an extract of walnut for rheumatoid arthritis was determined by using a rat with adjuvant arthritis. As an adjuvant, a suspension manufactured by Difco in which dead dry cells of *Mycobacterium butyricum* are suspended at 1% concentration in fluid paraffin was used. Then, by injecting 50 μl of the adjuvant under the plantar skin of a right hind leg of a male Fisher rat, arthritis was induced. 3 Weeks later, the left hind leg which has not been injected with an adjuvant (that is, leg without inflammation) was stretched 5 times, and only the rat showing 5 times a screaming reaction was used for the following test. An extract of walnut extracted with various alcohol concentrations (that is, extract of branches or shells) was administered either by oral administration or topical injection. As a result, it was found that the walnut extraction solution has a therapeutic effect for rheumatoid arthritis.

INDUSTRIAL APPLICABILITY

The present invention may be used for a pharmaceutical industry, a food product industry, and a cosmetic product manufacturing industry.

The invention claimed is:

1. A method for treating obesity comprising a step of administering an antiobesity agent which comprises an extract of onigurumi (Juglans sieboldiana Maxim), himegurumi (Juglans subcordiformis Dode), or shinanogurumi (Juglans regia L.) branches.

2. The method according to claim 1, wherein the extract of onigurumi (Juglans sieboldiana Maxim), himegurumi (Juglans subcordiformis Dode), or shinanogurumi (Juglans regia L.) branches is an alcohol extract of onigurumi (Juglans sieboldiana Maxim), himegurumi (Juglans subcordiformis Dode), or shinanogurumi (Juglans regia L.) branches.

3. The method according to claim 1, wherein the treating obesity is preventing an increase in neutral fat amount, cholesterol amount, fat amount, or body weight.

4. The method according to claim 1, wherein the treating obesity is inhibiting a binding between synoviolin and PGC-1β.

5. The method according to claim 1, wherein the treating obesity is inhibiting ubiquitination of PGC-1β by synoviolin.

* * * * *